United States Patent
Yoshioka et al.

(10) Patent No.: US 11,647,932 B2
(45) Date of Patent: May 16, 2023

(54) BIOSENSOR AND METHOD OF MANUFACTURING THE SAME

(71) Applicant: Nitto Denko Corporation, Ibaraki (JP)

(72) Inventors: Ryoma Yoshioka, Ibaraki (JP); Hiroki Senda, Ibaraki (JP)

(73) Assignee: NITTO DENKO CORPORATION, Ibaraki (JP)

( * ) Notice: Subject to any disclaimer, the term of this patent is extended or adjusted under 35 U.S.C. 154(b) by 24 days.

(21) Appl. No.: 17/285,272

(22) PCT Filed: Oct. 11, 2019

(86) PCT No.: PCT/JP2019/040245
§ 371 (c)(1),
(2) Date: Nov. 11, 2021

(87) PCT Pub. No.: WO2020/080297
PCT Pub. Date: Apr. 23, 2020

(65) Prior Publication Data
US 2022/0071539 A1 Mar. 10, 2022

(30) Foreign Application Priority Data

Oct. 17, 2018 (JP) .............................. JP2018-195820
Sep. 27, 2019 (JP) .............................. JP2019-177232

(51) Int. Cl.
*A61B 5/00* (2006.01)
*A61B 5/257* (2021.01)

(52) U.S. Cl.
CPC ............ *A61B 5/257* (2021.01); *A61B 5/6833* (2013.01); *A61B 2562/125* (2013.01); *A61B 2562/164* (2013.01)

(58) Field of Classification Search
CPC .. A61B 5/257; A61B 5/6833; A61B 2562/164
See application file for complete search history.

(56) References Cited

U.S. PATENT DOCUMENTS 9,119,578 B2 9/2015 Haghgooie et al.
2003/0069510 A1 4/2003 Semler
(Continued)

FOREIGN PATENT DOCUMENTS

CN 102892356 A 1/2013
CN 103747723 A 4/2014
(Continued)

OTHER PUBLICATIONS

International Search Report issued for corresponding International Patent Application No. PCT/JP2019/040245 dated Dec. 17, 2019, along with an English translation.
(Continued)

*Primary Examiner* — Adam Z Minchella
(74) *Attorney, Agent, or Firm* — Hauptman Ham, LLP

(57) ABSTRACT

A biosensor having a satisfactory wearing comfort is provided, taking the compressive elastic modulus, the thickness and the planar area of the component into account. The biosensor includes a substrate having a rigidity K of 3.0 N·mm² or less expressed by following formula (1), and a component provided on a first main surface of the substrate, the component having a rigidity that satisfies following formula (2) and is equal to or greater than a predetermined value, $$K = ET^3/12 \quad (1)$$

$$K \leq 6.34 \times 10^{14} \times S^{-10.6} \quad (2)$$

where E and T in formula (1) denote a compressive elastic modulus at 23° C. expressed in megapascals (MPa), and a thickness expressed in millimeters (mm), respectively. In formula (2), K denotes the rigidity expressed by formula (1) in newton millimeters squared (N·mm²), and S denotes a planar area expressed in square centimeters (cm²).

3 Claims, 5 Drawing Sheets

(56) References Cited

U.S. PATENT DOCUMENTS

| | | | |
|---|---|---|---|
| 2005/0096513 A1* | 5/2005 | Ozguz | H01L 21/6836 600/301 |
| 2005/0101875 A1 | 5/2005 | Semler et al. | |
| 2008/0146958 A1* | 6/2008 | Guillory | A61B 5/4094 600/544 |
| 2012/0165759 A1 | 6/2012 | Rogers et al. | |
| 2013/0041235 A1* | 2/2013 | Rogers | H05K 1/0283 600/386 |
| 2014/0163342 A1 | 6/2014 | Shimuta et al. | |
| 2020/0397326 A1* | 12/2020 | Rogers | A61B 5/4821 |

FOREIGN PATENT DOCUMENTS

| | | |
|---|---|---|
| JP | H5-329123 A | 12/1993 |
| JP | 2012-10978 A | 1/2012 |
| JP | 2013-514146 A | 4/2013 |
| JP | 2014-516644 A | 7/2014 |
| WO | 2012/149134 A1 | 11/2012 |

OTHER PUBLICATIONS

Written Opinion issued for corresponding International Patent Application No. PCT/JP2019/040245 dated Dec. 17, 2019.

The explanation of circumstances concerning accelerated examination filed for corresponding Japanese Patent Application No. 2019-177232 on May 20, 2020, along with an English translation.

Office Action issued for corresponding Japanese Patent Application No. 2019-177232 dated Jul. 7, 2020, along with an English machine translation.

Office Action issued for corresponding Japanese Patent Application No. 2019-177232 dated Dec. 15, 2020, along with an English machine translation.

Office Action issued for corresponding Chinese Patent Application No. 201980067875.4 dated Aug. 4, 2021, along with an English machine translation.

Decision to Grant issued for corresponding Japanese Patent Application No. 2019-177232 dated Mar. 30, 2021, along with an English machine translation.

Extended European Search Report dated May 31, 2022 for corresponding European Patent Application No. 19874310.6.

\* cited by examiner

FIG.2A
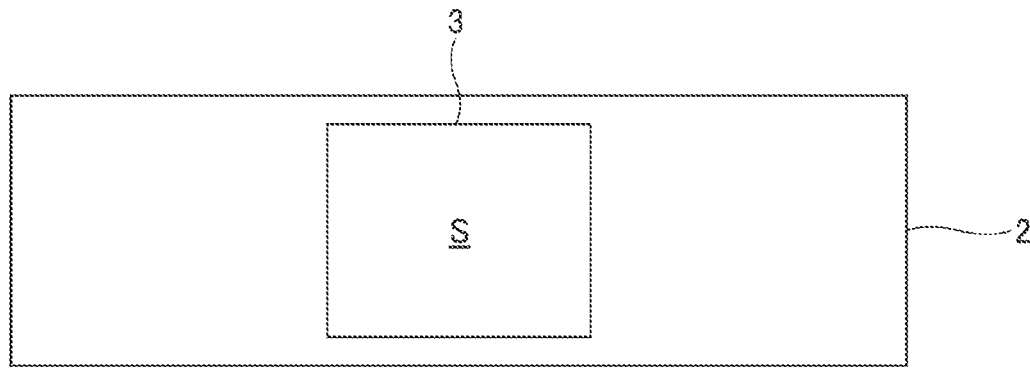
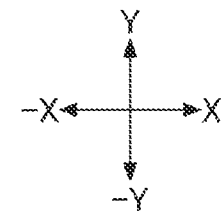
FIG.2B
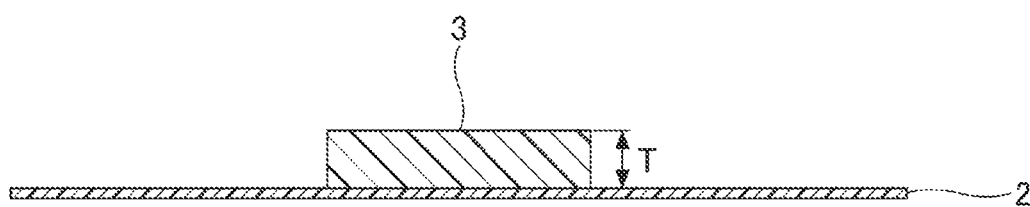
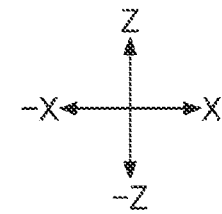

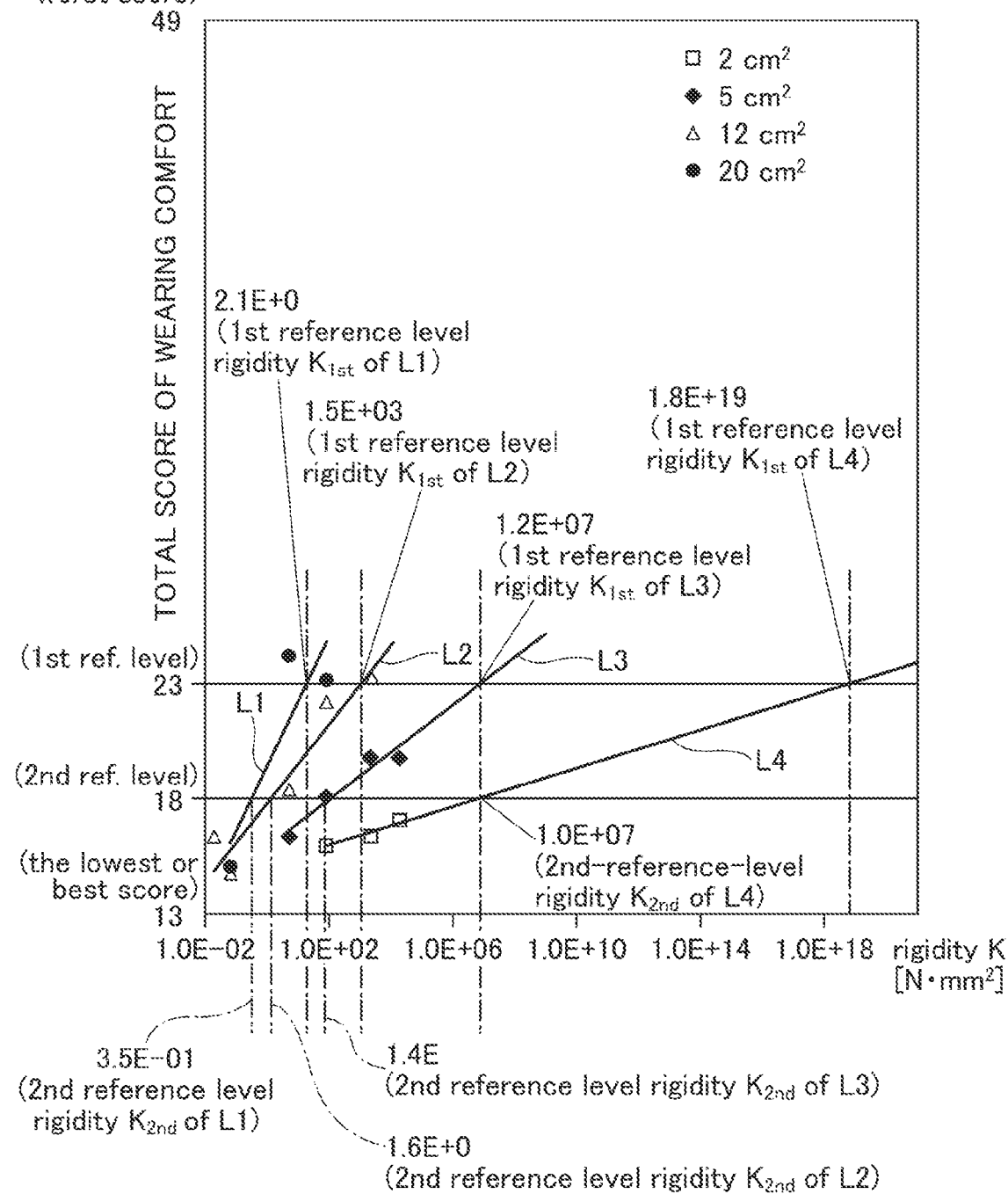

FIG. 5

| sample group | COMPONENT material | PHYSICAL PARAMETERS OF COMPONENT | | | | EVALUATION average score of wearing comfort | REFERENCE-LEVEL RIGIDITY (K') [N·mm²] | |
|---|---|---|---|---|---|---|---|---|
| | | plane area S [cm²] | compressive elastic modulus E [MPa] | thickness T [mm] | rigidity K [N·mm²] | | 1st ref. level rigidity $K_{1st}$ | 2nd ref. level rigidity $K_{2nd}$ |
| 1st sample group | test material 1 | 2 | 1.0 | 1 | 8.3E+01 | 16 | 1.8E+19 | 1.0E+07 |
| | test material 1 | | 1.0 | 3 | 2.3E+03 | 16 | | |
| | test material 1 | | 1.0 | 6 | 1.8E+04 | 17 | | |
| 2nd sample group | test material 1 | 5 | 1.0 | 0.4 | 5.3E+00 | 16 | 1.2E+07 | 1.4E+02 |
| | test material 1 | | 1.0 | 1 | 8.3E+01 | 18 | | |
| | test material 1 | | 1.0 | 3 | 2.3E+03 | 20 | | |
| | test material 1 | | 1.0 | 6 | 1.8E+04 | 20 | | |
| 3rd sample group | test material 1 | 12 | 1.0 | 0.4 | 5.3E+00 | 18 | 1.5E+03 | 1.6E+00 |
| | test material 1 | | 1.0 | 1 | 8.3E+01 | 22 | | |
| | test material 1 | | 1.0 | 3 | 2.3E+03 | 23 | | |
| | test material 2 | | 2.3E-05 | 3 | 2.0E-02 | 16 | | |
| | test material 2 | | 4.1E-05 | 3 | 7.0E-02 | 15 | | |
| 4th sample group | test material 1 | 20 | 1.0 | 0.4 | 5.3E+00 | 24 | 2.1E+01 | 3.5E-01 |
| | test material 1 | | 1.0 | 1 | 8.3E+01 | 23 | | |
| | test material 3 | | 4.1E-05 | 3 | 7.0E-02 | 15 | | |

BIOSENSOR AND METHOD OF MANUFACTURING THE SAME

CROSS REFERENCE TO RELATED APPLICATION

This application is a National Stage of International Application No. PCT/JP2019/040245, filed on Oct. 11, 2019, which designates the United States and was published in Japan, and which is based upon and claims priority to Japanese Patent Application Nos. 1) 2018-195820, filed on Oct. 17, 2018; and 2) 2019-177232, filed on Sep. 27, 2019 in the Japan Patent Office. All of the aforementioned applications are hereby incorporated by reference in their entireties.

TECHNICAL FIELD

The present invention relates to a biosensor and a method of manufacturing the same.

BACKGROUND ART

Conventionally, a self-adhesive biosensor attached to the surface of a living body has been known. For example, a biocompatible polymer substrate, which has a first layer made of a flexible polymer material, a second layer harder than the first layer, and a data acquiring module stacked in this order in the thickness direction, is proposed (see, for example, Patent Document 1 presented below).

SUMMARY OF THE INVENTION

Technical Problem to be Solved

When attached onto a living body, a biosensor should be comfortable to wear.

For instance, if the respective components used in the biosensor are flexible, satisfactory wearing comfort may be obtained. If the area of each component in the biosensor is small, satisfactory wearing comfort may also be obtained.

The second layer of the biocompatible polymer substrate used in Patent Document 1 has a large area, and is relatively hard. In this configuration, the wearing comfort may be impaired.

In addition, although the area of the data acquiring module in the biocompatible polymer substrate of Patent Document 1 is smaller than that of the second layer, the data acquiring module itself is hard and thick because it includes rigid materials. The wearing comfort is further impaired.

The present invention provides a biosensor, which imparts a satisfactory wearing comfort, taking the compressive elastic modulus, the thickness and the area of the component into account.

Technical Solution(s)

The inventors focused on the rigidity K, which is determined from the compressive elastic modulus E and the thickness T of a component provided on a substrate, and found the fact that good wearing comfort to a living body may be achieved when the rigidity K and the planar area S of the component satisfy a prescribed relationship. Hence, the present invention has been conceived.

Invention [1] provides a biosensor that includes a substrate having a rigidity K expressed by following formula (1), and a component provided on a first main surface of the substrate. The rigidity K of the substrate is 3.0 N·mm$^2$ or less. The component has a rigidity that satisfies following formula (2) and is equal to or greater than a predetermined value.

The formulae (1) and (2) are $$K = ET^3/12 \quad (1)$$

$$K \leq 6.34 \times 10^{14} \times S^{-10.6} \quad (2)$$

where E and T in formula (1) denote a compressive elastic modulus at 23° C. expressed in megapascals (MPa), and a thickness expressed in millimeters (mm), respectively. In formula (2), K denotes the rigidity expressed by formula (1) in newton millimeters squared (N·mm$^2$), and S denotes a planar area expressed in square centimeters (cm$^2$).

In this biosensor, the rigidity K of the substrate is sufficiently low, while the component has a certain degree of rigidity and satisfies formula (2) so as to have an appropriate rigidity according to the planar area S. Therefore, a satisfactory wearing comfort can be imparted to a living body.

Invention [2] provides the biosensor according to Invention [1], wherein the component includes a surface-mounted component provided on the substrate, and a sealing component that covers the surface-mounted component. The surface-mounted component has a planar area S1 of 10 [cm$^2$] or less, and a rigidity K1 of $1.0 \times 10^{-2}$ [N·mm$^2$] or higher. The sealing component has a planar area S2 of 15 [cm$^2$] or more, and a rigidity K2 of 3.0 [N·mm$^2$] or less.

In this biosensor, the surface-mounted component has a high rigidity K1 and a small planar area S1 so as not to impair the wearing comfort. The sealing component has a larger planar area S2 and a low rigidity K2 so as not to impair the wearing comfort. Therefore, the biosensor as a whole can provide a satisfactory wearing comfort to a living body.

Invention [3] provides a method of manufacturing a biosensor. The method includes a first step of preparing a substrate and a component, and a second step of providing the component onto a first main surface of the substrate. The substrate has a rigidity K of 3.0 N·mm$^2$ or less, the rigidity K of the substrate being expressed by following formula (1). The component has a rigidity that satisfies following formula (2) and is equal to or greater than a predetermined value.

Formulae (1) and (2) are $$K = ET^3/12 \quad (1)$$

$$K \leq 6.34 \times 10^{14} \times S^{-10.6} \quad (2)$$

where E and T in formula (1) denote a compressive elastic modulus at 23° C. expressed using in megapascals (MPa), and a thickness expressed in millimeters (mm), respectively. In formula (2), K denotes the rigidity expressed by formula (1) in newton millimeters squared (N·mm=), and S denotes a planar area expressed in square centimeters (cm$^2$).

With this method, a biosensor which imparts a satisfactory wearing comfort to a living body can be manufactured by preparing in the first step the substrate with a sufficiently low rigidity K and the component that satisfies formula (2) and is equal to or greater than a predetermined value. Then, the component is provided onto the substrate in the second step.

Advantageous Effect of the Invention

The biosensor and the method of manufacturing the biosensor according to the inventions can provide a satisfactory wearing comfort to a living body.

BRIEF DESCRIPTION OF DRAWINGS

FIG. 2A is a plan view showing a test example of the biological sensor;

FIG. 2B is a cross-sectional view of the test example of the biosensor;

FIG. 3 shows the relationship between rigidity K and score (average value) of wearing comfort;

FIG. 5 shows evaluation results of physical parameters of the respective sample groups.

DESCRIPTION OF PREFERRED EMBODIMENTS

Embodiment

<Self-Adhesive Biosensor>

Figure 1A:
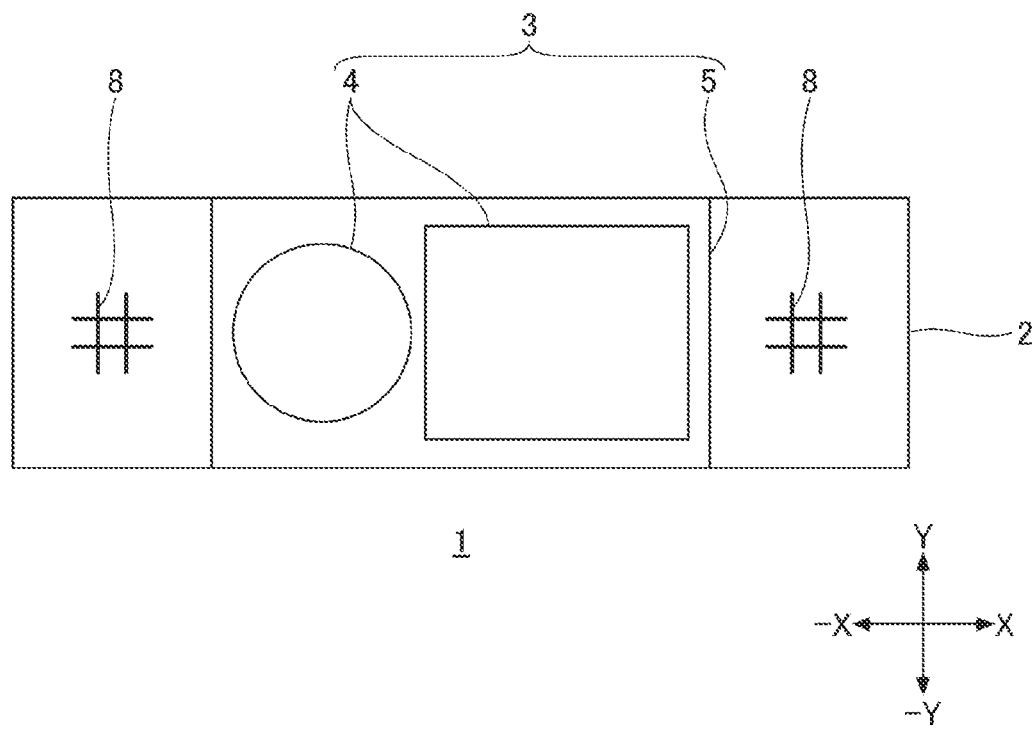
FIG. 1A is a plan view of a biosensor according to an embodiment of the invention.

A self-adhesive biosensor 1, which is an example of the biosensor according to the invention, will be described with reference to FIG. 1A and FIG. 1B.

The self-adhesive biosensor 1 is a sheet-like sensor having a substantially rectangular shape extending in a plane (e.g., in the X-Y plane). The thickness direction of the self-adhesive biosensor 1 is the Z direction.

The self-adhesive biosensor 1 has a substrate 2 and a component 3 provided on the substrate in the thickness direction (+Z direction).

<Substrate>

The substrate 2 serves as a support member that supports the self-adhesive biosensor 1, and also serves as an adhesive member that provides a pressure-sensitive adhesion (or adhesiveness) to the self-adhesive biosensor 1. The substrate 2 may be called a pressure-sensitive adhesive support.

The substrate 2 preferably has the largest planar area S, the lowest compressive modulus E, and the smallest thickness T in the self-adhesive biosensor 1. The rigidity K of the substrate 2 is preferably the lowest in the self-adhesive biosensor 1, as will be described later.

The substrate 2 has a first main surface 21, which is the top face of the substrate 2, and a second main surface 22, which is the back face of the substrate 2 when viewed in the thickness direction of the self-adhesive biosensor 1. The planar shape of the substrate 2 is substantially the same as that of the self-adhesive biosensor 1. Specifically, the substrate 2 is rectangular, and extends in the longitudinal direction (in the X direction of FIG. 1A and FIG. 1B) of the self-adhesive biosensor 1.

The substrate 2 includes, for example, a pressure-sensitive adhesive layer 6 and a support layer 7 provided on the pressure-sensitive adhesive layer 6, along the thickness direction (or the Z direction). The pressure-sensitive adhesive layer 6 provides the second main surface 22 of the substrate 2, which serves as the adhesive surface of the substrate 2. The support layer 7 provides the first main surface 21 of the substrate 2, which provides a support plane for supporting the component 3.

The pressure-sensitive adhesive layer 6 and the support layer 7 have almost the same planar shapes as the substrate 2.

The material of the pressure-sensitive adhesive layer 6 is, for example, a biocompatible pressure-sensitive adhesive, specifically, one selected so as to satisfy a rigidity K of the substrate described below. Examples of such pressure-sensitive adhesives include, but are not limited to acrylic pressure-sensitive adhesives, and silicone-based pressure-sensitive adhesives. Among these, acrylic pressure-sensitive adhesives are preferable.

The material of the support layer 7 is, for example, an elastic insulator, and specifically, one selected so as to satisfy the rigidity K of the substrate 2 described below. Examples of such an insulator include, but are not limited to polyurethane-based resins, silicone-based resins, acrylic-based resins, polystyrene-based resins, vinyl chloride-based resins, and polyester-based resins. Among these, polyurethane-based resins are preferable.

The rigidity K of the substrate 2 is 3.0 N·mm² or less, and preferably, $10^{-2}$ N·mm² or less. The rigidity K is more preferably $10^{-3}$ N·mm² or less, yet more preferably $10^{-4}$ N·mm² or less, and still more preferably $10^{-5}$ N·mm² or less. The rigidity of $5\times10^{-6}$ N·mm² or less is particularly preferable.

The rigidity K of the substrate 2 is expressed by formula (1).

$$K=ET^3/12 \quad (1)$$

where E denotes a compressive elastic modulus at 23° C. expressed in "MPa", and T denotes a thickness expressed in "mm".

If the rigidity K of the substrate 2 exceeds the above-described upper limit, the wearing comfort of the self-adhesive biosensor 1 with respect to a living body may be impaired.

Regarding the lower limit, the rigidity K of the substrate 2 may be, for example, $10^{-10}$ N·mm² or more, and preferably $10^{-9}$ N·mm⁻² or more. If the rigidity K of the substrate 2 is equal to or greater than the above-described lower limit, the mechanical strength of the self-adhesive biosensor 1 is sufficient, and the substrate 2 is easy to handle.

Because the rigidity K is determined by the compressive elastic modulus E and the thickness T, as defined in formula (1), the compressive elastic modulus E and the thickness T of the substrate 2 are selected such that the rigidity K falls within the above-described range.

Specifically, the compressive elastic modulus E of the substrate 2 at 23° C. represents a value measured for the combination of the pressure-sensitive adhesive layer 6 and the support layer 7 altogether. The value may be, for example, equal to or greater than 0.1 MPa, and 7000 MPa or less, preferably 3000 MPa or less.

The thickness T of the substrate 2 is the total thickness of the pressure-sensitive adhesive layer 6 and the support layer 7, which is, for example, 0.1 mm or less, preferably 0.01 mm or less, while being 0.1 μm or more, preferably 1.0 μm or more.

The ratio of the thickness of the pressure-sensitive adhesive layer 6 to the thickness of the support layer 7 ([thickness of layer 6]/[thickness of layer 7]) may be, for example, 0.5 or more, preferably greater than 1, more preferably 3 or more. Regarding the upper limit, the thickness ratio of the pressure-sensitive adhesive layer 6 to the support layer 7 may be 20 or less, and preferably 10 or less. Specifically, the thickness of the pressure-sensitive adhesive layer 6 may be, for example, 10 μm or more, preferably 20 μm or more, while the thickness of the pressure-sensitive adhesive layer 6 may be 95 μm or less, preferably 70 μm or less, and more preferably 50 μm or less. The thickness of the support layer 7 may be 1 μm or more, and preferably 5 μm or more, while the thickness of the support layer 7 may be 95 µm or less, preferably 50 µm or less, and more preferably 10 µm or less.

The planar area S of the substrate 2 can be appropriately designed in consideration of the size and the number of the components 3 mounted on the substrate 2, the handleability of the self-adhesive biosensor 1 when attached onto a living body, etc. Specifically, the planar area S of the substrate 2 may be, for example, 1 cm² or more, and preferably 10 cm² or more, while it is 1000 cm² or less, and preferably 250 cm² or less.

<Component>

The component 3 is arranged on the first main surface 21 of the substrate 2. The component 3 is positioned within the X-Y plane of the substrate 2 in a plan view. In this specification and claims, the "component" is one mounted on the substrate 2 and having a rigidity of a certain level or higher, more specifically, a component having a rigidity equal to or higher than the rigidity of the substrate 2. This is because a component harder than the substrate tends to ruin the wearing comfort of a wearable biosensor.

The compressive elastic modulus E and the thickness T of the component 3 are selected so as to satisfy a rigidity K described below. The component 3 preferably has a compressive elastic modulus E higher than that of the substrate 2, and/or a thickness T greater than that of the substrate 2. The component 3 may have a rigidity K higher than that of the substrate 2.

A plurality of components 3 may be arranged on the substrate 2. In the example of FIG. 1A and FIG. 1B, the components 3 include a surface-mounted component 4 provided on the substrate 2, and a sealing component 5 which seals the surface-mounted component 4.

Two or more surface-mounted components 4 are arranged on the first main surface 21 of the substrate 2 a certain interval between them along the longitudinal axis of the substrate 2.

Each of the surface-mounted components 4 has a relatively small planar area S1 among the components 3. The planar area S1 of the surface-mounted component 4 is, for example, 12.5 cm² or less, preferably 10 cm2 or less, more preferably 7.5 cm² or less, and still more preferably 5 cm² or less. Regarding the lower limit, the planar area S1 of the surface-mounted component 4 is 0.01 cm² or more, and preferably 0.1 cm² or more. The thickness T, the compressive elastic modulus E, and the rigidity K of the surface-mounted component 4 will be described in more detail later.

Examples of the surface-mounted component 4 include, but are not limited to an electronic circuit board (including a control circuit board), in which electronic devices such as a battery, a microcomputer chip, a memory, etc. are mounted on a hardboard, and a package board having the electronic circuit board packaged in a package. The surface-mounted components 4 provided on the substrate 2 are appropriately selected from the above-described examples. The shape of the surface-mounted component 4 is not particularly limited. Either a slightly thick circular shape (including a coin shape) or a thin rectangular shape (including a rectangular flat plate shape) may be employed.

The surface-mounted component 4 may also include a plurality of electrodes 8 which serve as sensors. Each of the electrodes 8 is embedded in the substrate 2 such that the electrode surface is exposed at the second main surface 22 of the substrate 2. Each of the electrodes 8 may have, for example, a grid shape formed of multiple conductive lines crossing each other in a bottom view of the substrate 2. In the self-adhesive biosensor 1, the electrodes 8 detect weak electrical bio-signals from the living body. The detected electrical signals are input to the control circuit board, processed using an electric power supplied from the battery, and stored as biological information in the memory.

Examples of the material of the surface-mounted component 4 include, but are not limited to hard materials such as ceramics, hard resin (specifically, ABS resin, acrylic resin, polyethylene terephthalate resin, etc.), and metals (good conductors such as copper).

The sealing component 5 may be, for example, a sealing layer that collectively covers and seals the surface-mounted components 4 (except for the electrodes 8) on the first main surface 21 of the substrate 2. The sealing layer has a sheet-like shape extending in the X-Y plane, and covers the top surfaces and the side surfaces of the surface-mounted components 4 on the substrate 2 to seal the surface-mounted components 4. It is unnecessary for the sealing component 5 to be in tight contact with the entire surface of each of the surface-mounted mounting component 4. The sealing component 5 may be a cover or a package that can internally accommodate the surface-mounted components 4 on the first main surface 21 of the substrate 2.

Among the plurality of components 3, the sealing component 5 has a relatively large planar area S2, which is greater than the planar area S1 of the surface-mounted component 4. The planar area S2 is, for example, greater than 12.5 cm², preferably 15 cm² or more, and more preferably 20 cm² or more, while it is equal to or less than 100 cm². The thickness T, compressive modulus E, and rigidity K of the sealing component 5 will be described in detail below. The thickness T of the sealing component 5 is the dimension from the top face of the substrate 2 to the top face of the sealing component 5.

Examples of the material of the sealing component 5 include, but are not limited to soft materials, specifically, elastic insulators (including insulative gels), and more specifically, materials softer than the hard material of the surface-mounted component 4. Such soft materials may be appropriately selected from the materials described above in connection with the substrate 2 so as to satisfy the physical properties of softness, elasticity, or electric insulation.

<Rigidity and Planar Area of Component>

In the self-adhesive biosensor 1, the component 3 satisfies the following formula (2).

$$K \leq 6.34 \times 10^{14} \times S^{-10.6} \quad (2)$$

where K is a rigidity represented by the above formula (1) and expressed in N·mm², and S is a planar area expressed in cm².

Specifically, when two or more components 3 are arranged on the substrate 2, each of the components 3 satisfies the formula (2).

More specifically, it is desirable that both the surface-mounted component 4 and the sealing component 5 satisfy the formula (2). In other words, a self-adhesive biosensor 1 in which the surface-mounted component 4 or the sealing component 5 does not satisfy the formula (2) may be excluded from the present invention, depending on the situation.

If the component 3 does not satisfy the formula (2), in other words, if $$K > 6.34 \times 10^{14} \times S^{-10.6}$$

holds, then the wearing comfort may be impaired.

The wearing comfort includes not only comfortable wearing feeling, but also discomfort due to pain, itching, skin tightness, rash, sweating or poor breathability, etc., or unpleasant feeling due to poor adhesion or separation of the self-adhesive biosensor.

The formula (2) is equivalent to following formula (4).

$$\text{Log } 10(K/6.34) \leq 14 \times S_{-10.6} \quad (4)$$

The domain of planar area S and the range of rigidity K that satisfy the formula (2) (and formula (4)) include the uppermost curve C1 and the hatched area below the curve C1 in FIG. 4.

Preferably, in the self-adhesive biosensor 1, both the surface-mounted component 4 and the sealing component 5 satisfy formula (3).

$$K \leq 2.97 \times 10^8 \times S^{-7.39} \quad (3)$$

When formula (3) is satisfied, better wearing comfort can be imparted to a living body. The formula (3) is equivalent to formula (5).

$$\text{Log } 10(K/2.97) \leq 8 \times S^{-7.39} \quad (5)$$

The domain of planar area S and the range of rigidity K that satisfy the formula (3) (and formula (5)) include curve C2 plotted in the middle among the three curves in FIG. 4 and the area below the curve C2.

Meanwhile, it is also preferable to satisfy the following formula (6).

$$K \geq 325 \times S^{-5} \quad (6)$$

Figure 4:
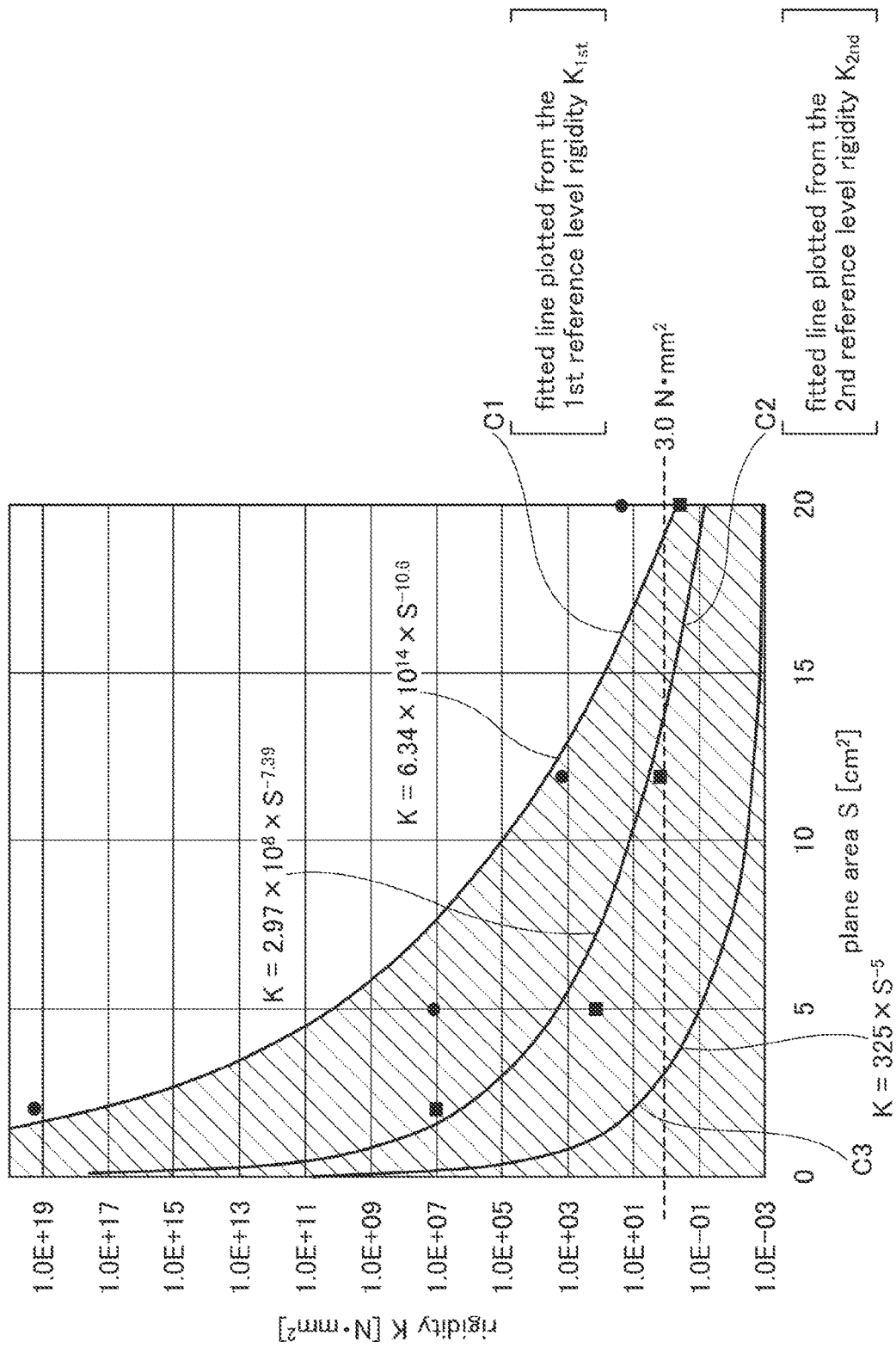
FIG. 4 shows the relationship between planar area S and rigidity K.

The domain of planar area S and the range of rigidity K that satisfy formula (6) include the lowermost curve C3 and the area above the curve C3 in FIG. 4.

If the formula (6) is satisfied under the condition that formula (1) is also satisfied, then each component 3 has sufficient rigidity, and simultaneously, the self-adhesive biosensor 1 can impart a satisfactory wearing comfort to the living body.

Specifically, the thickness T of the component 3 is, for example, 0.01 mm to 10 mm.

The compressive elastic modulus E of the component 3 at 23° C. is, for example, 100 MPa to 100,000 MPa.

The planar area S of the component 3 is, for example, 0.1 cm² to 500 cm².

In particular, when the component 3 includes a surface-mounted component 4 having a small planar area S1 (preferably 10 cm² or less) and a sealing component 5 having a planar area S2 larger than S1 of the surface-mounted component 4 (S2 being preferably 15 cm² or more), then the thickness T1 of the surface-mounted component 4 is preferably more than 2 mm, and the compressive elastic modulus E at 23° C. is preferably 10,000 MPa or higher. In this case, the rigidity K1 calculated from formula (2) may be $1.0 \times 10^{-2}$ [N·mm²] or higher, and even $1.0 \times 10^{-1}$ [N·mm²] or higher is acceptable.

The thickness T2 of the sealing component 5 is preferably 2 mm or less, and the compressive elastic modulus E at 23° C. of the sealing component 5 is preferably 5,000 MPa or less. The rigidity K2 calculated from formula (2) using the thickness T2 and the compressive elastic modulus E is 3.0 [N·mm²] or less, or $1.0 \times 10^{-3}$ [N·mm²] or less, or it may be reduced to as low as $1.0 \times 10^{-4}$ [N·mm²] or less.

<Derivation of Formulae for Rigidity and Planar Area>

The derivation of the above-described formulae is explained in detail below. Specific samples, numerical values, and other factors are also described in detail later, based on actual examples.

First, a substrate 2 and a plurality of components 3 are prepared.

Then, as illustrated in FIG. 2A and FIG. 2B, the components 3 are arranged onto the first main surface 21 of the substrate 2. Multiple samples of the self-adhesive biosensor 1 are fabricated. Among the multiple samples, the substrates 2 are the same, namely, only one type of substrate 2 is used for the multiple samples.

As shown in FIG. 5, those samples that have the same planar area S, but have different values of thickness T and/or compressive elastic modulus E are grouped in the same sample group.

The samples included in the same sample group have different rigidities K for the components 3 because the thickness T and/or the compressive elastic modulus E of the components 3 is/are different from one another.

A plurality of sample groups are prepared, each of the sample groups having a different planar area S of the component 3.

Then, each sample is attached onto the skin of a human body. Specifically, the second main surface 22 (i.e., the pressure-sensitive adhesive layer 6) of the substrate 2 is attached onto the skin.

For each of the samples, uncomfortable feelings caused by five factors, namely, pain/itch, skin tightness, rash, sweating/poor breathability, and separation/poor adhesion are scored. Specifically, each of the five factors of the wearing comfort is evaluated by 1 to 4 scores, or 1 to 3 scores, and the total score of the five factors is calculated. One sample is tested on a plurality of subjects (the number n of the subjects is two or more), and the average value of the total scores acquired from the plurality of subjects is calculated.

The average scores are classified for each sample group (i.e., each group with the same planar area S of the component 3), and then, the average scores of the respective samples in each sample group are plotted as a function of rigidity K, as illustrated in FIG. 3.

To be more precise, for the respective samples having the components 3 with the same planar area S, the average scores of the wearing comfort are plotted on the chart of FIG. 3, in which the horizontal axis represents rigidity K and the vertical axis represent score of wearing comfort. Then, lines are fitted with the data points of the respective sample groups to acquire approximate lines L (lines L1 to L4 in this example). After that, the intersection of each approximate line L and each of the two levels of the reference score of the wearing comfort is specified to determine the reference-level rigidity K' (including the first reference-level rigidity $K_{1st}$ and the second reference-level rigidity $K_{2nd}$). The reference level of the wearing comfort is such a score that imparts a satisfactory wearing comfort to living bodies if the score is at or below that level, while the wearing comfort is impaired if the score exceeds that level. As shown in FIG. 3 and FIG. 5, each sample group has a rigidity K' denoted by the first reference-level rigidity $K_{1st}$ and the second reference-level rigidity $K_{2nd}$. Particular examples of the reference score and the reference-level rigidity K' are explained later.

The procedure of acquiring a reference-level rigidity K' for a sample group is carried out for all the sample groups. As a result, each of the sample groups acquires the reference-level rigidity K' including the first and second reference-level rigidities $K_{1st}$ and $K_{2nd}$.

Then, as shown in FIG. 4, the reference-level rigidity K' (including the first and second reference-level rigidities) are plotted as a function of planar area S, with the horizontal axis representing the planar area S and the vertical axis representing the rigidity K.

Then, approximate curves C (including C1 and C2) are drawn by fitting a line with the data points of each of the first and second reference-level rigidities. Thus, formulas (2) and (3) expressing the fitted lines C1 and C2, respectively, are obtained.

<Manufacturing Process of Biosensor>

Next, a manufacturing process of the self-adhesive biosensor 1 is described.

The method of manufacturing the self-adhesive biosensor 1 includes a first step and a second step carried out in this order.

In the first step, a substrate 2 having a rigidity K of 3.0 N·mm² or less, and a component 3 having a predetermined rigidity which satisfies the formula (2) are prepared.

In this first step, a substrate 2 having a planar area S and a rigidity K which satisfy the formula (2) is selected.

Then, assuming that the component 3 includes a surface-mounted component 4 and a sealing component 5, the materials of the surface-mounted component 4 and the sealing component 5 are selected such that each of the surface-mounted component 4 and the sealing component 5 has a predetermined compressive elastic modulus E. Subsequently, the thicknesses T of the surface-mounted component 4 and the sealing component 5 are determined. By substituting the values of the compressive elastic modulus E and the thickness T for formula (1), the rigidity K is obtained for each of the surface-mounted component 4 and the sealing component 4. After that, the planar area S is determined for each of the components 3 so as to satisfy the formula (2).

In the second step, the components 3 are provided onto the first main surface 21 of the substrate 2.

Specifically, the surface-mounted component 4 is placed on the first main surface 21 of the substrate 2, and then the sealing component 5 is arranged so as to cover the first main surface 21 and the periphery of the substrate 2. As a result, the surface-mounted component 4 is covered and sealed with the sealing component 5. The electrodes 8 may be arranged on the second main surface 22 of the base material 2. A through-hole penetrating through the substrate 2 may be formed to provide the electrodes 8 at the second main surface 22, and then the remaining space in the through-hole may be filled with the material of the substrate 2.

In this manner, a self-adhesive biosensor 1 is fabricated.

In the self-adhesive biosensor 1, the rigidity K of the substrate 2 is sufficiently low, and the component 3, which has a rigidity K in accordance with the planar area S, satisfies the formula (2). Accordingly, a satisfactory wearing comfort to a living body can be achieved.

In the self-adhesive biosensor 1, rigidity K1 of the surface-mounted component 4 may be high, but the planar area S1 is small, so that the wearing comfort is not impaired. The sealing component 5 has a larger planar area S compared with the surface-mounted component 4, while the rigidity K2 is low, so that the wearing comfort is maintained. Consequently, a satisfactory wearing comfort can be imparted to the living body.

With the manufacturing method of the self-adhesive biosensor 1, a substrate 2 having a sufficiently low rigidity K and a component 3 satisfying the formula (2) are prepared in the first step, and the component 3 is arranged onto the substrate 2 in the second step. This method can produce a self-adhesive biosensor 1 which can impart a satisfactory wearing comfort to the living body.

<Modifications>

Modifications of the above-described configuration or process, in which the same elements as those in the above-described embodiment may be denoted by the same reference numerals and redundant descriptions may be omitted, are also included in the present invention. Two or more modifications may be mutually combined. Each modification provides the same technical effect as that of the above-described embodiment, unless otherwise noted.

A living body may be either a human body or a non-human creature. The living body is preferably a human body.

In the above-described embodiment, in preparation of the component 3 in the first step, compressive elastic modulus E, thickness T, and planar area S are determined in this order as the physical parameters or properties of the component 3. However, the invention is not limited to this procedure as long as the component 3 satisfies formula (2). For instance, the planar area S may be determined first, and then, the compressive elastic modulus E and the thickness T may be determined one by one in this order or in reverse order, or the compressive elastic modulus E and the thickness T may be simultaneously determined.

ACTUAL EXAMPLES

The present invention is further described below, based on specific examples and comparative examples, which do not limit the present invention. Specific numerical values, including a composition ratio (or content ratio), or physical properties or parameters presented in the following examples may be substituted for those values of the corresponding composition ratio (or content ratio), or physical properties or parameters already described above as criteria including or not including the upper limit (defined as "at or below" or "smaller (less) than") or the lower limit (defined as "at or above" or "greater (higher) than").

Test Example 1: Derivation of Formula (2)

A base material 2 and multiple components 3 are prepared.

The substrate 2 is formed of "Soft-Skin Permirol (registered trademark) Lite" (polyurethane resin, manufactured by Nitoms Inc.), and has a thickness T of 0.008 mm, a planar area S of 50 cm², and a compressive elastic modulus E of 25 MPa.

The material and physical parameters of the components 3 are shown in FIG. 5. Particulars of the test materials 1 to 3 in FIG. 5 are as follows.

Test Material 1: ABS resin

Test Material 2: Elastic gel, polyurethane resin, hardness is 0, model number HO-100 (manufactured by EXSEAL Co., Ltd.)

Test Material 3: Elastic gel, polyurethane resin, hardness is 7, model number H5-100 (manufactured by EXSEAL Co., Ltd.)

The number after "E+" or "E−" in the column of rigidity K in FIG. 5 represents an exponent (or power) of 10. For example, "8.3E+01" represents "8.3×10¹". This notation applies to the signed symbols "E+" and "E−" used in FIG. 3 and FIG. 4.

Then, the components 3 are arranged on the first main surfaces 21 of the substrates 2, as illustrated in FIG. 2A and FIG. 2B, to fabricate a plurality of samples.

As shown in FIG. 5, samples having components 3 with the same planar areas S are classified in the same sample group. Specifically in Test Example 1, three samples with components 3 whose planar area S is 2 cm² are grouped in the first sample group. Four samples with components 3 whose planar area S is 5 cm² are grouped in the second sample group. Five samples with components 3 whose planar area S is 12 cm² are grouped in the third sample group. Three samples with components 3 whose planar area S is 20 cm² are grouped in the fourth sample group.

As many samples as the number "n" (three in this example) of human subjects to be tested are fabricated for each sample type.

Subsequently, the respective (three) samples of the same type were attached to the skins of the three human subjects (n=3) to be tested. Then, each of the following items (of wearing comfort) was evaluated for each subject, and scores of the respective items of wearing comfort were collected from each subject. Because the indexes "itch/pain" and "rash" particularly affect the wearing comfort, the scores of these items are multiplied by five (i.e., weighting factor 5), and the scores of all the indexes are summed up to calculate the total score. FIG. 5 shows the average of the total score of wearing comfort of the three human subjects.

Allocation of marks for each evaluation item is as follows.
(Itch/Pain)
  4 points: sore
  3 points: itchy
  2 points: prickly
  1 point: not bothering
(Skin Tightness)
  3 points: feel tight during both rest and exercise
  2 points: not tight during exercise but tight during rest
  1 point: not bothering in either rest or exercise
(Rash)
  4 points: rash on the skin
  3 points: marks on the skin
  2 points: skin reddish
  1 point: no abnormality
(Sweating/Poor Breathability)
  3 points: uncomfortable and unbearable
  2 points: uncomfortable, but still bearable
  1 point: not bothering
(Separation/Poor Adhesion)
  3 points: completely came off
  2 points: partially came off
  1 point: did not come off In the five evaluation items, the lowest score is 13 points total (1×5 points in itch/pain, 1 point in skin tightness, 1×5 points in rash, 1 point in sweating/poor breathability, and 1 point in separation/poor adhesion), which imparts the best wearing comfort. The highest score is 49 points total (4×5 points in itch/pain, 3 points in skin tightness, 4×5 points in rash, 3 points in sweating/poor breathability, and 3 point in separation/poor adhesion), in which the wearing comfort is most impaired.

The evaluation results are shown in FIG. 5, with average scores of the wearing comfort collected from three human subjects. The evaluations of the respective samples in each of the first to the fourth sample groups are then plotted as shown in FIG. 3, in which the horizontal axis represents rigidity K, and the vertical axis represents the total score of wearing comfort (the average of three human subjects).

Then, lines L (thick solid lines sloping upward toward the right-hand side) are fitted with the data points plotted for the respective sample groups. Four approximate lines L1 to L4 are drawn corresponding to the first to the fourth sample groups.

Then, the intersections of the four approximate lines L1 to L4 and the first reference level of the wearing comfort are specified, and the first reference-level rigidity $K_{1st}$ is determined at each of the intersections.

In the Test Example 1, the first reference level is set to 23 points. The first reference level is determined by adding 10 points to the lowest score (13 point). The value 10 points is about 28% of the difference (36 points) between the lowest store (13 points) and the highest scores (49 points). Value (13 points+10 points). At or below the first reference level, the sample imparts a satisfactory wearing comfort to a living body.

One sample group has one first reference-level rigidity $K_{1st}$. Specifically, as shown in FIG. 5, the first sample group has the first reference-level rigidity $K_{1st}$ of $1.8 \times 10^{19}$ N·mm², the second sample group has the first reference-level rigidity $K_{1st}$ of $1.2 \times 10^{7}$ N·mm², the third sample group has the first reference-level rigidity $K_{1st}$ of $1.5 \times 10^{3}$ N·mm², and the fourth sample group has the first reference-level rigidity $K_{1st}$ of 2.1 N·mm².

Then, as shown in FIG. 4, the first reference rigidities $K_{1st}$ of the first to the fourth sample groups are plotted as a function of planar area S on a chart with the horizontal axis of planar area S and the vertical axis of rigidity K. the vertical axis. In this Test Example 1, four points were plotted on the chart.

Then, an approximate curve C1 is acquired by fitting a line with the four plotted points, and formula (2) that expresses the approximate curve C1 is obtained.

$$K \leq 6.34 \times 10^{14} \times S^{-10.6} \quad (2)$$

Test Example 2: Derivation of Formula (3)

The same procedure as in the Test Example 1 is carried out, except that the second reference-level rigidities $K_{2nd}$ are acquired, in place of the first reference-level rigidities $K_{1st}$, for the first to the fourth sample groups, as shown in FIG. 3. In this test example, the second reference level, whose requirement for wearing comfort is stricter than that of the first reference level, is adopted. The second reference level is set to 18 points. The value 18 points is determined by adding 5 points, which is about 14% of the difference between the lowest points (13 points) and the highest points (49 points), to the lowest point (13 points). At or below the second reference level, the sample imparts better wearing comfort to a living body.

One sample group has one second-level rigidity $K_{2nd}$, and the first to the fourth sample groups have their own values of the second-level rigidity, as shown in FIG. 5.

An approximate curve C2 is plotted by fitting a line with the data points of the second-level rigidities of the first to the fourth sample group, as shown in FIG. 4, and formula (3) expressing the approximate curve C2 is acquired. living body includes.

Practical Example 1

Figure 1B:
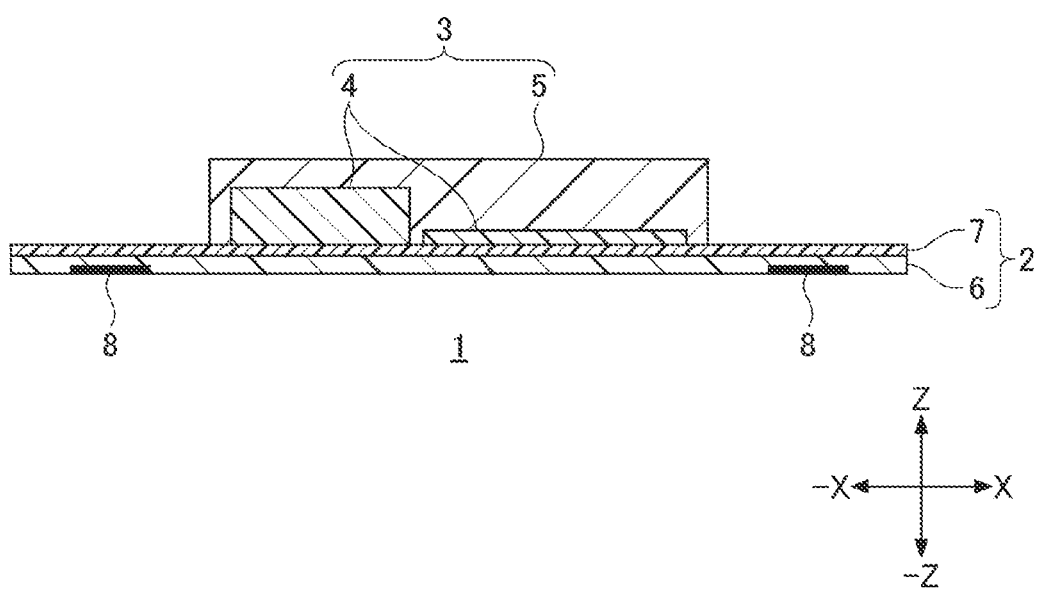
FIG. 1B is a cross-sectional view of the biosensor according to the embodiment.

A self-adhesive biosensor 1 having a substrate 2 and two or more components 3 arranged on one surface of the substrate 2, as illustrated in FIG. 1A and FIG. 1B, was prepared.

The components 3 includes a surface-mounted component 4 assembled with a battery and a substrate package, and a sealing component 5 formed of a sealing layer.

The substrate 2 is formed of "Soft-Skin Permirol (registered trademark) Lite" (polyurethane resin, manufactured by Nitoms Inc.), and has a thickness T of 0.1 mm, a planar area S of 30 cm², and a compressive elastic modulus E of 25 MPa. By substituting the values of the compressive elastic modulus E and the thickness T into formula (1), the rigidity K of $1.1 \times 10^{-6}$ of the substrate 2 was determined. The rigidity K of $1.1 \times 10^{-6}$ of the substrate 2 was within the range of 3.0 N·mm2 or less.

The battery (used as the surface-mounted component 4) is rigid, and it is assumed that the thickness T is 2 mm, that the planar area S is 3.1 cm², and that the compressive elastic modulus E is 200,000 MPa, which is the compressive elastic modulus of stainless steel used as the hardest material in the battery. By substituting the values of the compressive elastic modulus E and the thickness T into formula (1), a rigidity K of $1.3\times10^5$ N·mm2 was determined. Then, the values of the rigidity K and the planar area S of the battery (namely, the surface-mounted component 4) were substituted into formula (2). The calculated result satisfied the inequality of formula (2).

The substrate package (used as the surface-mounted component 4) is rigid, and has a thickness T of 0.3 mm, a planar area S of 7.5 cm², and a compressive elastic modulus E of 3,000 MPa. The values of the compressive elastic modulus E and the thickness T were substituted into the formula (1) to calculate the rigidity K, which was 6.8 N·mm². Then, the values of the rigidity K and the planar area S of the substrate package (as the surface-mounted component 4) were substituted into formula (2). The calculated result satisfied the inequality of formula (2).

The sealing layer (serving as the sealing component 5) is formed of a soft polyurethane resin. The thickness T of the sealing layer is 3 mm, the planar area S is 16.5 cm², and the compressive elastic modulus E is 0.04 MPa. The compressive elastic modulus E and the thickness T were substituted into formula (1), and a rigidity K of 0.00009 N·mm² was calculated. Then, the values of the rigidity K and the planar area S of the sealing layer (as the sealing component 5) were substituted into formula (2). The calculated result satisfied the inequality of formula (2).

The substrate 2 satisfied formula (1), and both the surface-mounted component 4 and the sealing component 5 satisfied formula (2).

When this sample of the self-adhesive biosensor 1 was attached onto the skin of a human body, satisfactory wearing comfort was achieved.

Comparative Example 1

The same procedure as in Practical Example 1 was carried out, except that the battery (i.e., the surface-mounted component 4) did not satisfy the formula (1), to fabricate a comparative sample of the self-adhesive biosensor 1. When this comparative sample was attached onto the skin of the human body, the wearing comfort was impaired.

To be more specific, the thickness T of the battery (as the surface-mounted component 4) is 2 mm, and the planar area S is of the battery is 12 cm². When rigidity K was calculated using formula (1), and when the values of the rigidity K and the planar area S were substituted into formula (2), then the left-hand side of formula (2) became greater than the right-hand ($K>6.34\times10^{14}\times S^{10.6}$). The inequality of formula (2) was not satisfied.

Comparative Example 2

The same procedure as in Practical Example 1 was carried out, except that the substrate package (serving as the surface-mounted component 4) did not satisfy the formula (1), to fabricate a comparative sample of the self-adhesive biosensor 1. When this comparative sample was attached onto the skin of the human body, the wearing comfort was impaired.

To be more specific, the planar area S of the substrate package (as the surface-mounted component 4) was 30 cm², which was too large. When the values of the rigidity K calculated from formula (1) and the planar area S of this comparative example were substituted into formula (2), then the left-hand side of formula (2) became greater than the right-hand. The inequality of formula (2) was not satisfied.

Comparative Example 3

The same procedure as in Practical Example 1 was carried out, except that the sealing layer (serving as the sealing component 5) did not satisfy the formula (1), to fabricate a comparative sample of the self-adhesive biosensor 1. When this comparative sample was attached onto the skin of the human body, the wearing comfort was impaired.

To be more specific, the compressive elastic modulus E of the sealing layer (as the sealing component 5) was 1,000 MPa, which was too great, and the rigidity K calculated from formula (1) was 2250 N·mm². The values of the rigidity K and the planar area S of the sealing layer were substituted into formula (2), then the left-hand side of formula (2) became greater than the right-hand. The inequality of formula (2) was not satisfied.

Comparative Example 4

The same procedure as in Practical Example 1 was carried out, except that the thickness T of the battery (as the surface-mounted component 4) did not satisfy the formula (1), to fabricate a comparative sample of the self-adhesive biosensor 1. When this comparative sample was attached onto the skin of the human body, the wearing comfort was impaired.

To be more specific, the thickness of the battery (as the surface-mounted component 4) was 80 mm, which was too thick, and the rigidity K calculated from formula (1) was $8.5\times10^9$ N·mm². The values of the rigidity K and the planar area S of the sealing layer were substituted into formula (2), then the left-hand side of formula (2) became greater than the right-hand. The inequality of formula (2) was not satisfied.

LISTING OF SYMBOLS

1: self-adhesive biosensor
2: substrate
3: component
4: surface-mounted component
5: sealing component
21: first main surface
22: second main surface

PRIOR ART DOCUMENT(S)

Patent Document: Japan Patent Application Laid-open Publication No. 2012-10978

What is claimed is:

1. A biosensor comprising:
    a substrate having a rigidity K expressed by following formula (1), the rigidity K of the substrate being 3.0 N·mm² or less, the substrate including a support layer that configures a first main surface of the substrate and a pressure-sensitive adhesive layer that configures a second main surface, opposite to the first main surface, of the substrate;
    a component provided on the first main surface of the substrate, the component including an electronic circuit board mounted on the first main surface of the substrate and sealed with a sealing component: wherein the component, the electronic circuit board, and the sealing component have a respective rigidity and a respective planar area that satisfies following formulas (2), (3) and (4); and an electrode provided in the pressure-sensitive adhesive layer so that a surface of the electrode is exposed at the second main surface, wherein $$K = ET^3/12 \tag{1}$$

$$K \leq 6.34 \times 10^{14} \times S^{-10.6} \tag{2}$$

$$K \geq 325 \times S^{-5} \tag{3}$$

$$K \leq 2.97 \times 10^8 \times S^{-7.39} \tag{4}$$

where E and T in formula (1) denote a compressive elastic modulus at 23° C. expressed in megapascals (MPa), and a thickness expressed in millimeters (mm), respectively, and in formulas (2), (3) and (4), K denotes the rigidity expressed by formula (1) in newton millimeters squared (N·mm²), and S denotes the planar area expressed in square centimeters (cm²), and the electronic circuit board has a planar area S1 of 10 [cm²] or less and a rigidity K1 of $1.0 \times 10^{-2}$ [N·mm²] or higher, and the sealing component has a planar area S2 of 15 [cm²] or more and a rigidity K2 of 3.0 [N·mm²] or less.

2. The biosensor as claimed in claim 1,
wherein the rigidity of the electronic circuit board is equal to or higher than the rigidity of the substrate.

3. A method of manufacturing a biosensor, comprising:
a first step of preparing a substrate having a rigidity K of 3.0 N·mm² or less expressed by following formula (1), the substrate including a support layer that configures a first main surface and a pressure-sensitive adhesive layer that configures a second main surface opposite to the first main surface, and preparing a component including an electronic circuit board mounted on the first main surface of the substrate and sealed with a sealing component; wherein the component, the electronic circuit board, and the sealing component have a respective rigidity and a respective planar area that satisfies following formulas (2), (3) and (4);

$$K = ET^3/12 \tag{1}$$

$$K \leq 6.34 \times 10^{14} \times S^{-10.6} \tag{2}$$

$$K \geq 325 \times S^{-5} \tag{3}$$

$$K \leq 2.97 \times 10^8 \times S^{-7.39} \tag{4}$$

where E and T in formula (1) denote a compressive elastic modulus at 23° C. expressed in megapascals (MPa), and a thickness expressed in millimeters (mm), respectively, and in formulas (2), (3) and (4), K denotes the rigidity expressed by formula (1) in newton millimeters squared (N·mm²), and S denotes the planar area expressed in square centimeters (cm²); and a second step of providing the component onto the first main surface of the substrate, and providing an electrode in the pressure-sensitive adhesive layer so that a surface of the electrode is exposed at the second main surface, wherein the electronic circuit board has a planar area S1 of 10 [cm²] or less and a rigidity K1 of $1.0 \times 10^{-2}$ [N·mm²] or higher, and the sealing component has a planar area S2 of 15 [cm²] or more and a rigidity K2 of 3.0 [N·mm²] or less.

* * * * *